(12) United States Patent
Johnson

(10) Patent No.: US 6,582,689 B1
(45) Date of Patent: Jun. 24, 2003

(54) IL-18/IGIF CHEMOTHERAPEUTIC COMPOSITIONS

(75) Inventor: Randall K. Johnson, Ardmore, PA (US)

(73) Assignee: Smithkline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/700,609

(22) PCT Filed: May 20, 1999

(86) PCT No.: PCT/US99/11160

§ 371 (c)(1),
(2), (4) Date: Nov. 17, 2000

(87) PCT Pub. No.: WO99/59565

PCT Pub. Date: Nov. 25, 1999

Related U.S. Application Data

(60) Provisional application No. 60/086,560, filed on May 21, 1998.

(51) Int. Cl.[7] .................. A61K 45/00; A61K 38/00; C07K 1/00; C07K 14/00; C07K 17/00
(52) U.S. Cl. ............... 424/85.2; 424/85.1; 530/351; 514/2; 514/12
(58) Field of Search ............... 424/1.41, 85.1, 424/85.2; 435/69.1, 69.5, 69.51, 69.52, 69.6, 332, 335, 337, 375; 514/2, 12, 21, 44; 530/350, 351, 324, 388.2, 388.23

(56) References Cited

U.S. PATENT DOCUMENTS

| | | | | |
|---|---|---|---|---|
| 5,728,687 A | * | 3/1998 | Bissery | 514/151 |
| 5,869,535 A | * | 2/1999 | Pezzuto et al. | 514/640 |
| 6,207,641 B1 | * | 3/2001 | Torigoe et al. | 514/12 |

FOREIGN PATENT DOCUMENTS

| | | |
|---|---|---|
| EP | 0 712 931 | 5/1996 |
| EP | 0 767 178 | 4/1997 |
| EP | 0 845 530 | 6/1998 |

OTHER PUBLICATIONS

Susan G. Arbuck, "Clinical Status and Optimal Use of Topotecan", *Oncology*, 11(11): 1635–1651, 1997.

de Jonge, et al., "The Development of Combination Therapy Involving Camptothecins: A Review of Preclinical and Early Clinical Studies", *Cancer Treatment Reviews*, 24: 205–220, 1998.

Osaki, et al., "IFN–γ–Inducing Factor/IL–18 Administration Mediates IFN–γ– and IL–12– Independent Antitumor Effects". *The Journal of Immunology*, 160: 1742–1749 (1998).

* cited by examiner

*Primary Examiner*—James Housel
*Assistant Examiner*—Zachariah Lucas
(74) *Attorney, Agent, or Firm*—Elizabeth J. Hecht; Edward R. Gimmi; Charles M. Kinzig

(57) ABSTRACT

The present invention relates generally to compositions comprising potentiators, such as IL-18, also known as interferon-γ-inducing factor (IGIF), in combination with a chemotherapeutic agent, processes for making such compositions, the use of such compositions for the prevention and/or treatment of cancer, and the use of such compositions to inhibit the growth of tumors or cancerous cells in mammals.

5 Claims, 12 Drawing Sheets

IL-18: ug/animal, ip, Days 11-15, 18-48
Topotecan:mg/kg, ip, Days 11,15,19,24,29,34,39,44
CR=complete regression, PR=partial regression
LTR=Long-term regression (Day 90)

IL-18:ug/animal, ip, Days 11-15, 18-48
Topotecan:mg/kg, ip, Days 11,15,19,23,29,34,39,44
CR=complete regression, PR=partial regression
LTR=Long-term regression Day 90

—○— Topotecan 9
—○— Control
—●— Topo 9/IL-18 10; 5 CR, 1PR 2/7 LTR
—■— Topo 9/IL-18 3.0
—♦— Topo 9/IL-18 1.0
—▲— Topo 9/IL-18 0.3

IL-18: ug/mouse, ip, Days 10-39
LTR=Long-term remission Day 112

—●— IL-18 100 ug 4/7 CR, 4/7 LTR
—■— IL-18 30 ug 0/7 CR
—♦— IL-18 10 ug 1/7 CR
—▲— IL-18 3 ug 0/7 CR
—▼— IL-18 1 ug 0/7 CR
—⊞— Control IL18:sc, ug/mouse, Day 10,14,18,22,26
Topotecan: ip, mg/kg, Days 10,14
CR= complete regression; PR= partial regression; LTR= Long-term regression

- IL18: 1000ug; 1/6CR, 1/6 LTR
- IL18: 100ug; 1/6CR, 1/6 LTR
- IL18: 10ug; 1/6CR, 1/6 LTR
- IL18/Topo: 1000/15 Toxic
- IL18/Topo: 100/15 ; 4/6CR, 2/6 LTR
- IL18/Topo: 10/15; 4CR 1PR/6, 1/6 LTR
- Topotecan: 15; 3/6CR, 1/6 LTR
- Control IL-18: ip Days 11-15, and 18-22

CPA: ip, Day 11 and 18
IL-18: ip, Days 11-15, 18-22, and 25

- ▲ 300 mg/kg CPA + 0.3 ug IL-18
- ♦ 300 mg/kg CPA + 1 ug IL-18
- ■ 300 mg/kg CPA + 3 ug IL-18
- ● 300 mg/kg CPA + 10 ug IL-18
- ○ 300 mg/kg CPA
- ⊞ Control Topotecan: mg/kg, ip, Days 11, 15, 19
IL-18: ug/mouse, if, Days 11-15, 18-22

- ▲ Topo 15/IL-18 0.3
- ♦ Topo 15/IL-18 1.0
- ■ Topo 15/IL-18 3.0
- ● Topo 15/IL-18 10
- ○ Topo 15
- ⊞ Control

IL-18/IGIF CHEMOTHERAPEUTIC COMPOSITIONS

This is a 371 of International Application PCT/US99/11160, filed May 20, 1999, which claims benefit from the following Provisional Applications No. 60/086,560 filed May 21, 1998.

FIELD OF THE INVENTION

The present invention relates generally to compositions comprising a potentiator such as IL-18, also known as interferon-γ-inducing factor (IGIF), and chemotherapeutic agents. The chemotherapeutic agents may be, for example, camptothecins such as topotecan, anthracycline antibiotics such as doxorubicin, alkylating agents such as cyclophosphamide, or antimicrotubule agents such as paclitaxel. The present invention further relates to processes for making such compositions, the use of such compositions for the prevention and/or treatment of cancer, and the use of such compositions to inhibit the growth of tumors or cancerous cells in mammals.

BACKGROUND OF THE INVENTION

There have been significant advances in understanding the genetic and cellular changes that lead to cancer and that result in progression to more malignant and metastatic disease. There has been less impressive advances in therapy of metastatic cancer as many of the high-incidence tumors, such as colon, lung, prostate and breast cancer, either respond briefly or fail to respond at all to even the newest regimens of chemotherapeutic agents. The molecular biological studies of cancer have provided an understanding of the reasons why tumors fail to respond to chemotherapy. In normal cells, induction of DNA damage or other metabolic insult by chemotherapeutic agents turns on a programmed cell death pathway (apoptosis). As part of the genetic evolution of tumors, there is an upregulation of pathways that prevent apoptosis. This occurs as the result of selection for mutations, such as loss of p53 function or overexpression of bcl-2, that promote survival, since the aberrant DNA replication that occurs in cancer cells normally would trigger apoptosis. The fact that anti-apoptotic pathways are activated in tumor cells suggests that these cells will be refractory to many different chemotherapeutic agents, regardless of mechanism. Thus, it will be important to introduce new therapeutic modalities, such as inhibition of tumor-induced angiogenesis or stimulation of the immune response to tumors, to produce responses in chemorefractory cancers.

IL-18, also known as interferon-γ-inducing factor (IGIF), is a recently discovered novel cytokine. Active IL-18 contains 157 amino acid residues. It has potent biological activities, including induction of interferon-γ-production by T cells and splenocytes, enhancement of the killing activity of NK cells and promotion of the differentiation of naive $CD4^+T$ cells into Th1 cells. In addition, human IL-18 augments the production of GM-CSF and decreases the production of IL-10. IL-18 has been shown to have greater interferon-γ inducing capabilities than IL-12, and appears to have different receptors and utilize a distinct signal transduction pathway.

The therapeutic potentials for IL-18 in the treatment of cancer and for its antibody in the treatment of endotoxic shock induced liver damage (which is similar to human hepatic failure), have been evaluated in animal models, and protective effects have been demonstrated. For example, IL-18 has been reported to inhibit the metastasis and growth of colon 26 adenocarcinoma in mice. See, Hanaya, et al., Anti-tumor effect of a new cytokine, IGIF on the metastasis and growth of murine colon 26 adenocarcinoma. Proceeding of the American Association for Cancer Research 37: 451–452 (1996). Further studies regarding the anti-tumor activity of IL-18 have been reported in the following publications: Micallef et al., Interleukin 18 induces the sequential activation of natural killer cells and cytotoxic T Lymphocytes to protect syngeneic mice from transplantation with Meth A sarcoma, *Cancer Res.* 57:4557–4563 (1997); Yoshida et al., Antitumor effect of human pancreatic cancer cells transduced with cytokine genes which activate Th1 helper T cells, *Anticancer Res.* 18:333–336, (1998); Osaki et al., IFN-γ-inducing factor/IL-18 administration mediates IFN-γ- and IL-12-independent antitumor effects, *J. Immunol.* 160:1742–1749 (1998); and Micallef et al., Augmentation of in vitro interleukin 10 production after in vivo administration of interleukin 18 is activated macrophage-dependent and is probably not involved in the antitumor effects of interleukin 18, *Anticancer Res.* 18(6A):4267–74 (1998).

$CD4^+T$ cells are the central regulatory elements of all immune responses. They are divided into two subsets, Th1 and Th2. Each subset is defined by its ability to secrete different cytokines. Interestingly, the most potent inducers for the differentiation are cytokines themselves. The development of Th2 cells from naive precursors is induced by IL4. Prior to the discovery of IL-18, IL-12 was thought of as the principal Th1 inducing cytokine. IL-18 is also a Th1 inducing cytokine and is more potent than IL-12 in stimulating the production of interferon-γ.

Th1 cells secrete IL-2, interferon-γ, and TNF-β. Interferon-γ, the signature Th1 cytokine, acts directly on macrophages to enhance their microbiocidal and phagocytic activities. As a result, the activated macrophages can efficiently destroy intracellular pathogens and tumor cells. The Th2 cells produce IL-4, IL-5, IL-6, IL-10 and IL-13, which act by helping B cells develop into antibody-producing cells. Taken together, Th1 cells are primarily responsible for cell-mediated immunity, while Th2 cells are responsible for humoral immunity IL-18, the encoding nucleotide sequence, and certain physicochemical chemical properties of the purified protein is known.

Kabushiki Kaisha Hayashibara Seibutsu Kayaku Kenkyujo's ("Hayashibara"), EP 0692536 A2, published on Jan. 17, 1996, discloses a mouse protein which induces IFN-gamma production by immunocompetent cells, the protein being further characterized as having certain physicochemical properties and a defined partial amino acid sequence. Also disclosed is a protein having a 157 aa sequence, two fragments thereof, DNA (471 bp) encoding the protein, hybridomas, protein purification methods, and methods for detecting the protein.

Hayashibara's EP 0712931 A2, published on May 22, 1996, discloses a 157 aa human protein and homologues thereof, DNA encoding the protein, transformants, processes for preparing the protein, monoclonal antibodies against the protein, hybridomas, protein purification methods, and methods for detecting the protein.

Hayashibara's EP 0767178 A1, published on Apr. 9, 1997, discloses a human protein having a 10 aa sequence near the N-terminus and which induces the interferon gamma production by an immunocompetent cell. Also disclosed are processes for producing the protein, the protein as a pharmaceutical agent, use of the protein as an antioncotic agent, antitumor agent, antiviral agent, antibacterial agent, immunopathy agent and for treatment of atopic diseases.

Incyte Pharmaceuticals, Inc.'s, WO 97/24441, published on Jul. 10, 1997, discloses a 193 aa protein corresponding to IL-18 precursor and encoding DNA.

Chemotherapeutic agents are known in the art. For example, camptothecins, including topotecan, are disclosed in SmithKline Beecham Corporation's, U.S. Pat. No. 5,004,758 (758 patent), issued on Apr. 2, 1991. Camptothecins, including topotecan, are also disclosed in *Cancer Chemotherapy and Biotherapy, second edition*, edited by Bruce A. Chabner and Dan L. Longo, Lippincott-Raven Publishers, Philadelphia © 1996. pp. 463–484. Topotecan is disclosed in The Merck Index, Twelfth Edition, © 1996 Merck & Co., Inc. under monograph number 9687. Anthracycline antibiotics, including doxorubicin, are disclosed in *Cancer Chemotherapy and Biotherapy, second edition*, edited by Bruce A. Chabner and Dan L. Longo, Lippincott-Raven Publishers, Philadelphia © 1996. pp. 409–434. Doxorubicin is disclosed in The Merck Index, Twelfth Edition, © 1996 Merck & Co., Inc. under monograph number 3495. Alkylating agents, including cyclophosphamide, are disclosed in *Cancer Chemotherapy and Biotherapy, second edition*, edited by Bruce A. Chabner and Dan L. Longo, Lippincott-Raven Publishers, Philadelphia © 1996. pp. 297–332. Cyclophosphamide is disclosed in The Merck Index, Twelfth Edition, © 1996 Merck & Co., Inc. under monograph number 2816. Antimicrotubule agents, including paclitaxel, are disclosed in *Cancer Chemotherapy and Biotherapy, second edition*, edited by Bruce A. Chabner and Dan L. Longo, Lippincott-Raven Publishers, Philadelphia © 1996. pp. 263–296. Paclitaxel is disclosed in The Merck Index, Twelfth Edition, © 1996 Merck & Co., Inc. under monograph number 7117. Other chemotherapeutic agents are known to those skilled in the art.

SUMMARY OF THE INVENTION

In one aspect, the present invention provides a polypeptide having at least 70% identity of the amino acid sequence of SEQ ID NO:1 or SEQ ID NO:2 over the entire length of the sequences in combination with a chemotherapeutic agent.

In another aspect, the present invention provides a polypeptide having at least 70% identity of the amino acid sequence of SEQ ID NO:1 or SEQ ID NO:2 over the entire length of the sequences in combination with a chemotherapeutic agent including, preferably, a camptothecin, such as topotecan, an anthracycline antibiotic, such as doxorubicin, an alkylating agent such as cyclophosphamide, or an antimicrotubule agent such as paclitaxel. More preferably, the chemotherapeutic agent is topoisomerase. Most preferably, the chemotherapeutic agent is topotecan. Combinations of the polypeptide with other chemotherapeutic agents known to those skilled in the art are also encompassed by this invention.

In yet another aspect, the present invention provides a pharmaceutical composition comprising a polypeptide, such as IL-18, a chemotherapeutic agent, and a pharmaceutically acceptable carrier.

In a further aspect, the present invention provides a process for preparing the composition described above comprising combining the polypeptide with the chemotherapeutic agent and recovering the resulting composition.

In a further aspect, the present invention provides a method of preventing and/or treating cancer in a mammal comprising the administration of a cancer inhibiting amount of a composition comprising a polypeptide, such as IL-18, and a chemotherapeutic agent.

In a further aspect, the present invention provides a method of preventing and/or treating cancer in a mammal comprising the administration of a cancer inhibiting amount of a composition comprising a polypeptide, such as IL-18, and a chemotherapeutic agent, and a pharmaceutically acceptable carrier.

In another aspect, the present invention provides a method of inhibiting the growth of tumor cells in a mammal sensitive to a composition comprising a polypeptide, such as IL-18, and a chemotherapeutic agent, wherein such method comprises administering to a mammal afflicted with said tumor cells, an effective, tumor cell growth inhibiting amount of such composition.

In another aspect, the present invention provides a method of inhibiting the growth of tumor cells in a mammal sensitive to a composition comprising a polypeptide, such as IL-18, and a chemotherapeutic agent, and a pharmaceutically acceptable carrier, wherein such method comprises administering to a mammal afflicted with said tumor cells, an effective, tumor cell growth inhibiting amount of such composition.

DETAILED DESCRIPTION OF THE INVENTION

Figure 1:
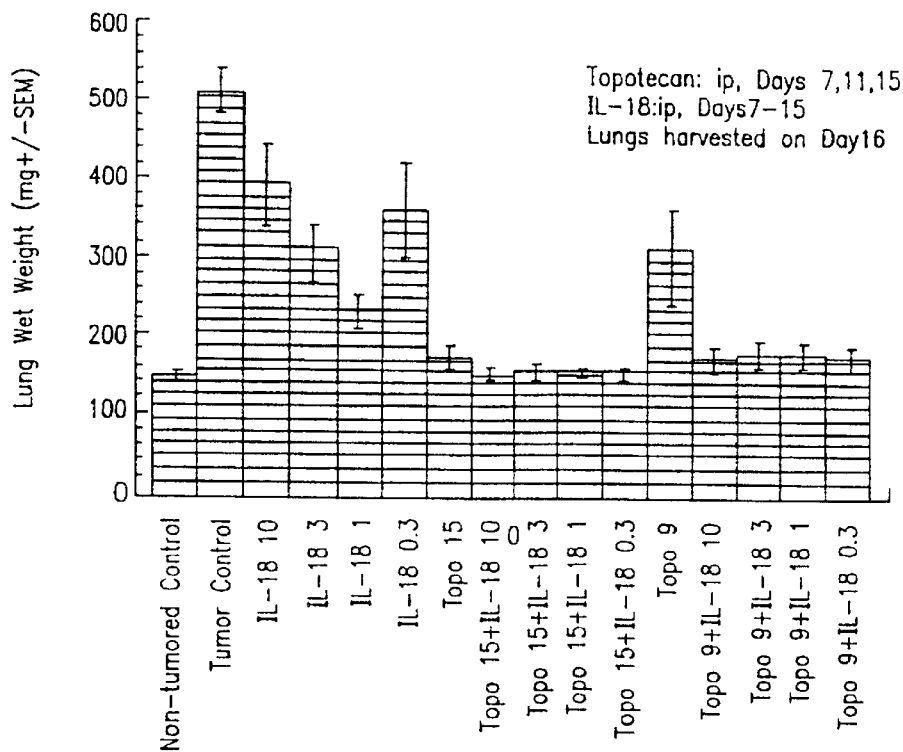
FIG. 1 is a graph illustrating the effect of IL-18 alone and in combination with topotecan on growth of advanced pulmonary Lewis lung carcinoma.

The present invention relates generally to compositions comprising a potentiator such as IL-18 and chemotherapeutic agents. The chemotherapeutic agents may be, for example, camptothecins such as topotecan, anthracycline antibiotics such as doxorubicin, alkylating agents such as cyclophosphamide, or antimicrotubule agents such as paclitaxel. The present invention further relates to processes for making such compositions, the use of such compositions for the prevention and/or treatment of cancer, and methods for inhibiting the growth of tumors or cells.

The following definitions are provided to facilitate understanding of certain terms and abbreviations used frequently in this application.

"CPA" means cyclophosphamide; "CR" means complete regression; "ip" means intraperitoneal; "iv" means intravenous; "ILS" means increased life span; "LTR" means long term regression; "MTD" means maximum tolerated dosage; "PR" means partial regression; "q1D" means one dose every day; "q4D" means one dose every 4 days; "q4D×6" means one dose every 4 days times 6; "q4D×7" means one dose every 4 days times 7; "qD×5" means one dose every day for 5 days; "qD×21" means one dose every day for 21 days; "qD×26" means one dose every day for 26 days; "qD×30" means one dose every day for 30 days; "sc" means subcutaneous; "UID" means one dose per day.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., J. Mol. Biol. 215: 403–410 (1990). The well known Smith Waterman algorithm may also be used to determine identity.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, PROTEINS—STRUCTURE AND MOLECULAR PROPERTIES, 2nd Ed., T. E. Creighton, W. H. Freeman and Company, New York, 1993; Wold, F., Post-translational Protein Modifications: Perspectives and Prospects, pgs. 1–12 in POST-TRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Post-translational Modifications and Aging", Ann NY *Acad Sci* (1992) 663:48–62).

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

Preferred parameters for polypeptide sequence comparison include the following:
1) Algorithm: Needleman and Wunsch, J. Mol Biol. 48: 443–453 (1970)

Comparison matrix: BLOSSUM62 from Hentikoff and Hentikoff, Proc. Nati. Acad. Sci. USA. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

A polypeptide sequence of the present invention may be identical to the reference sequence of SEQ ID NO:1 or SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:1 or SEQ ID NO:2 by the numerical percent of the respective percent identity (divided by 100) and then subtracting that product from said total number of amino acids in SEQ ID NO:1 or SEQ ID NO:2, respectively, or:

$$n_a \leq x_a - (x_a \cdot y),$$

wherein $n_a$ is the number of amino acid alterations, $x_a$ is the total number of amino acids in SEQ ID NO:1 or SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

"Fusion protein" refers to a protein encoded by two, often unrelated, fused genes or fragments thereof. In one example, EP-A-0 464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharnacokinetic properties [see, e.g., EP-A 0232 262]. On the other hand, for some uses it would be desirable to be able to delete the Fc part after the fusion protein has been expressed, detected and purified.

Potentiators

Potentiators in general enhance the immune response in combination with a cytoreductive therapy. IL-18 is a broad range potentiator that maintains its immunostimulatory action when combined with different types of chemotherapeutic agents. Certain potentiatiors of chemotherapeutic agents are specific and are related to the mechanism of action of the drug being modulated, such as the use of leucovorin in combination with 5-fluorouracil or the use of tirapazamine with DNA damaging agents such as cisplatin or alkylating agents.

IL-18 Polypeptide

In one aspect, the present invention relates to IL-18 polypeptides in combination with a chemotherapeutic. The polypeptide component of the polypeptide and camptothecin compound containing compositions of the present invention, its isolation, identification and certain techniques of production are disclosed in EP 0692536A2, EP 0712931A2, EP0767178A1, and WO 97/2441. The polypeptides include isolated polypeptides comprising an amino acid sequence which has at least 70% identity, preferably at least 80% identity, more preferably at least 90% identity, yet more preferably at least 95% identity, most preferably at least 97–99% identity, to that of SEQ ID NO:1 (human IL-18) and SEQ ID NO:2 (murine IL-18) over the entire length of SEQ ID NO:1 and SEQ ID NO:2, respectively. Such polypeptides include those comprising the amino acid of SEQ ID NO:1 and SEQ ID NO:2, respectively.

Polypeptides of the present invention are interferon-γ-inducing polypeptides. They play a primary role in the induction of cell-mediate immunity, including induction of interferon-γ production by T cells and spleenocytes enhancement of the killing activity of NK cells and promotion of the differentiation of naive CD4+T cells into Th1 cells. These properties are hereinafter referred to as "IL-18 activity" or "IL-18 polypeptide activity" or "biological activity of IL-18". Also included amongst these activities are antigenic and immunogenic activities of said IL-18 polypeptides, in particular the antigenic and immunogenic activities of the polypeptides of SEQ ID NO:1 and SEQ ID NO:2. Preferably, a polypeptide of the present invention exhibits at least one biological activity of IL-18.

The polypeptides of the present invention may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Recombinant polypeptides of the present invention may be prepared by processes well known in the art from genetically engineered host cells comprising expression systems. Accordingly, in a further aspect, the present invention relates to expression systems which comprises a polynucleotide or polynucleotides encoding the polypeptides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

Representative examples of appropriate hosts include bacterial cells, such as *streptococci, staphylococci, E. coli, Streptomyces* and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., Molecular Cloning: A Laboratory Manual, 2nd Ed., Cold Spring Harbor Laboratory Press, Cold Spring Harbor, N.Y. (1989). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, high performance liquid chromatography, hydroxylapatite chromatography and lectin chromatography. Most preferably, affinity chromatography is employed for purification. Well-known techniques for refolding proteins may be employed to regenerate active conformation when the polypeptide is denatured during isolation and or purification.

Chemotherapeutic Agents

The invention contemplates the use of any categories of chemotherapeutic agents in combination with a potentiator, for example IL-18. Examples of categories of chemotherapeutic agents are, camptothecins such as topotecan, anthracycline antibiotics such as doxorubicin, alkylating agents such as cyclophosphamide, and antimicrotubule agents such as paclitaxel. More preferably, the chemotherapeutic agent is topoisomerase. Most preferably, the chemotherapeutic agent is topotecan. Other chemotherapeutic agents known to those skilled in the art are also encompassed by this invention.

Examples of chemotherapeutic agents known in the art are camptothecins. Topotecan is an example of camptothecins. Camptothecins, including topotecan, are disclosed in SmithKline Beecham Corporation's 758 patent, issued on Apr. 2, 1991. Camptothecins, including topotecan, are also disclosed in *Cancer Chemotherapy and Biotherapy, second edition*, edited by Bruce A. Chabner and Dan L. Longo, Lippincott-Raven Publishers, Philadelphia © 1996. pp. 463–484. Topotecan is further disclosed in The Merck Index, Twelfth Edition, © 1996 Merck & Co., Inc. under monograph number 9687.

Another example of chemotherapeutic agents known in the art are anthracycline antibiotics. Doxorubicin and daunorubicin are examples of anthracycline antibiotics. These agents are some of the most widely used antineoplastic agents in current clinical practice. Doxorubicin is currently used principally for the treatment of solid tumors, especially breast cancer and lymphoma. See *Cancer Chemotherapy and Biotherapy, second edition*, edited by Bruce A. Chabner and Dan L. Longo, Lippincott-Raven Publishers, Philadelphia © 1996. pp. 409–434. Doxorubicin is further disclosed in The Merck Index, Twelfth Edition, © 1996 Merck & Co., Inc. under monograph number 3495.

Alkylating agents are another example of chemotherapeutic agents known in the art. An example of an alkylating agent is cyclophosphamide. These agents are used extensively in chemotherapy, both in conventional combination regiments and in high-dose protocols with bone marrow transplantation. See, *Cancer Chemotherapy and Biotherapy, second edition*, edited by Bruce A. Chabner and Dan L.

Longo, Lippincott-Raven Publishers, Philadelphia © 1996. pp. 297–332. Cyclophosphamide is further disclosed in The Merck Index, Twelfth Edition, © 1996 Merck & Co., Inc. under monograph number 2816.

Antimicrotubule agents are another category of chemotherapeutic agents known in the art. An example of an antimicrotubule agent is the taxane paclitaxel. Taxanes are effective in a broad range of tumor types. See, *Cancer Chemotherapy and Biotherapy, second edition*, edited by Bruce A. Chabner and Dan L. Longo, Lippincott-Raven Publishers, Philadelphia © 1996. pp. 263–296. Paclitaxel is further disclosed in The Merck Index, Twelfth Edition, © 1996 Merck & Co., Inc. under monograph number 7117.

The present invention provides for a combination of potentiators such as the IL-18 polypeptides described above, and chemotherapeutic agents known in the art, for example, the ones discussed above.

In a further aspect, the present invention provides for pharmaceutical compositions comprising a therapeutically effective amount of a potentiator, as described above, in combination with a chemotherapeutic agent, as described above. Pharmaceutically acceptable carriers or excipients may also be employed. The pharmaceutical carrier employed may be, for example, either a solid or a liquid. Exemplary of solid carriers include, but are not limited to lactose, terra alba, sucrose, talc, gelatin, agar, pectin, acacia, magnesium stearate, stearic acid and the like. Exemplary of liquid carriers include, but are not limited to, saline, buffered saline, dextrose, water, glycerol, ethanol syrup, peanut oil olive oil, and combinations thereof. Similarly, the carrier or diluent may include time delay material well known in the art, such as glyceryl monostearate or glyceryl distearate alone or with a wax ethylcellulose, hydroxypropylmethylcellulose, methylmethacrylate and the like.

The invention further relates to pharmaceutical packs and kits comprising one or more containers filled with one or more of the ingredients of the aforementioned compositions of the invention. The combination of polypeptides and chemotherapeutic agents may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. In addition, if the combination of polypeptide and chemotherapeutic agents can be formulated in an enteric or an encapsulated formulation, oral administration may be possible. Alternative means for systemic administration include transmucosal and transdermal administration using penetrants such as bile salts or fusidic acids or other detergents. Administration of these combinations may also be topical and/or localized, in the form of salves, pastes, gels, and the like.

The dosage range of the composition required depends on the choice of potentiator and chemotherapeutic agent, the route of administration, the nature of the formulation, the nature of the subject's condition, and the judgment of the attending practitioner. Suitable dosages of the composition, however, for IL-18 are in the range of 1 nanogram/kilogram to 1 milligran/kilogram of subject, and for the chemotherapeutic agent are in the range of 1/10 of the clinically accepted dosage for the specific chemotherapeutic agent to 10 times the clinically accepted dosage for the specific chemotherapeutic agent. Wide variations in the needed dosage, however, are to be expected in view of the variety of compounds available and the differing efficiencies of various routes of administration. For example, transdermal administration would be expected to require higher dosages than administration by intravenous injection. Variations in these dosage levels can be adjusted using standard empirical routines for optimization, as is well understood in the art.

The schedule for the administration of the composition depends on the dosage, on the choice of potentiator and chemotherapeutic agent, the route of administration, the nature of the formulation, the nature of the subject's condition, and the judgment of the attending practitioner. Suitable schedules for administration, however, are 1–3 dosages each day to 1 dosage each week. Wide variations in the schedules for the administration of the composition, however, are to be expected in view of the variety of compounds available and the differing efficiencies of various routes of administration. For example, transdermal administration would be expected to require higher dosages than administration by intravenous injection. Variations in these schedules for the administration of the composition can be adjusted using standard empirical routines for optimization, as is well understood in the art.

All publications, including but not limited to patents and patent applications, cited in this specification are herein incorporated by reference as if each individual publication were specifically and individually indicated to be incorporated by reference herein as though fully set forth.

It is believed that one skilled in the art can, using the preceding description, utilize the present invention to its fullest extent. The following Examples are, therefore, to be construed as merely illustrative and not a limitation of the scope of the present invention in any way.

EXAMPLE I (A)

Tumor Growth Reduction In Lewis Lung Carcinoma Model Experimental Protocol

Figure 2:
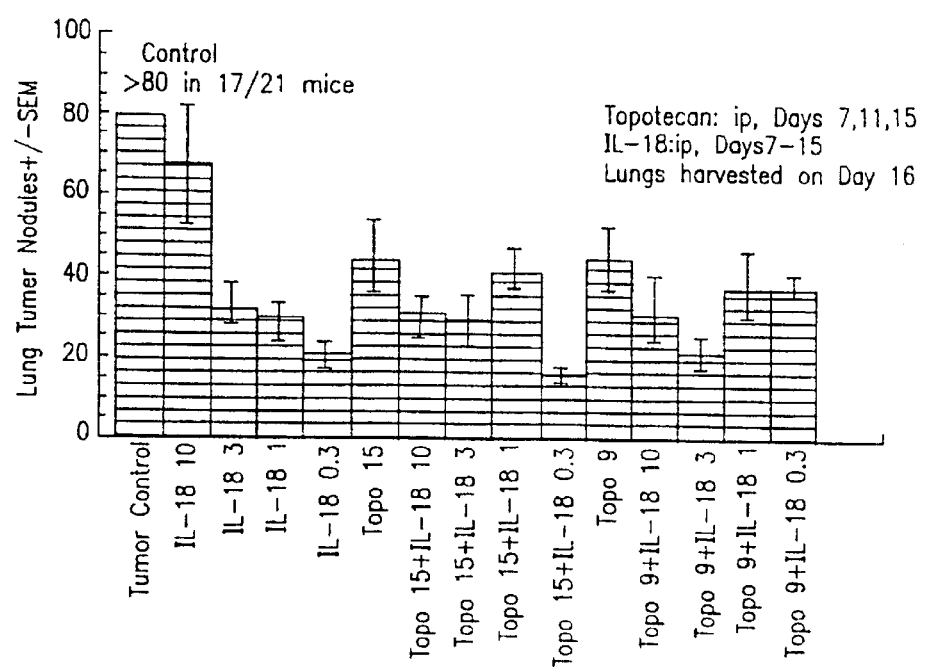
FIG. 2 is a graph illustrating the effect of IL-18 alone and in combination with topotecan on the number of Lewis lung carcinoma colonies in the lung.

In an experiment to show the activity of the combination of topotecan and IL-18 in advanced solid tumor model, highly metastatic Lewis lung carcinoma, $B6D2F_1$ female mice were inoculated intravenously with $10^5$ Lewis lung carcinoma cells and were randomized to treatment groups of 14 mice each on Day 7. Treatment was delayed until Day 7 when tumors were established and growing in the lungs. Half of the mice in each group were killed on Day 16 to determine effects of treatment on pulmonary tumor growth, the remaining mice were continued under treatment and monitored for survival. (See Example I (B)). Topotecan was administered intraperitonealy q4D×7 beginning on Day 7 and ending on Day 32 and the doses shown are in mg/kg. Murine IL-18 was administered intraperitonealy UID from Day 7 to Day 32 and the doses shown are µg/mouse. There were 3 groups of control animals, all of which died between Day 17 and 30. The animals were monitored for survival for 61 days. (See FIGS. 1 and 2 and Table 1).

Results

There was a very large tumor burden on Day 16 in the control group with an average of 350 mg of pulmonary tumor. (See FIGS. 1 and 2). The number of distinct macroscopic tumors in the lungs were >80. (See FIG. 2).

IL-18 alone significantly decreased the lung tumor weight and nodule count with no clear dose-response. The effect of IL-18 alone was only moderate and animals receiving the cytokine did not have an enhanced median survival time. An MTD of topotecan (15 mg/kg on a q4D regimen) suppressed tumor growth by >90% but mice still had an average of 45 pulmonary tumor nodules. The addition of IL-18 gave a similar strong tumor growth inhibition. However, there was a clear advantage for the combination at the suboptimal dose (9 mg/kg on a q4D regimen) of topotecan. (See FIGS. 1 and 2).

EXAMPLE I (B)

Survival In Lewis Lung Carcinoma Model

Experimental Protocol
See protocol for Example I (A).
Results

As shown in Table 1 below, the survival data from the trial of IL-18 in combination with topotecan in mice bearing advanced systemic Lewis lung carcinoma confirmed the activity of IL-18 that was observed by tumor measurements. As expected, IL-18, when used alone, had no effect on survival time. Topotecan alone prolonged lifespan by 68% at its MTD and by 63% at 0.6×MTD. IL-18 at 0.5 mg/kg+the MTD of topotecan (15 mg/kg) increased lifespan by 145%; a suboptimal dose of topotecan (9 mg/kg) coupled with IL-18 at 0.5 mg/kg increased lifespan by 82%.

TABLE 1

| Treatment | Dosage Level | Median Survival Time (days) | Increase in Lifespan (%) |
|---|---|---|---|
| Control | — | 22 | — |
| IL-18 | 10 | 24 | 9 |
|  | 3 | 23 | 4 |
|  | 1 | 22.5 | 2 |
|  | 0.3 | 22 | 0 |
| Topotecan | 15 | 37 | 68 |
| Topotecan + IL-18 | 15 + 10 | 54 | 145 |
|  | 15 + 3 | 32 | 45 |
|  | 15 + 1 | 47 | 114 |
|  | 15 + 0.3 | 41 | 86 |
| Topotecan | 9.0 | 36 | 63 |
| Topotecan + IL-18 | 9.0 + 10 | 40 | 82 |
|  | 9.0 + 3 | 38 | 73 |
|  | 9.0 + 1 | 35 | 59 |
|  | 9.0 + 0.3 | 28 | 27 |

Topotecan was administered intraperitonealy q4D × 7 beginning on Day 7 and ending on Day 32 and the doses shown are in mg/kg.
Murine IL-18 was administered intraperitonealy UID from Day 7 to Day 32 and the doses shown are μg/mouse.

EXAMPLE II (A)

Tumor Growth Reduction In Lewis Lung Carcinoma Model Experimental Protocol

Figure 3:
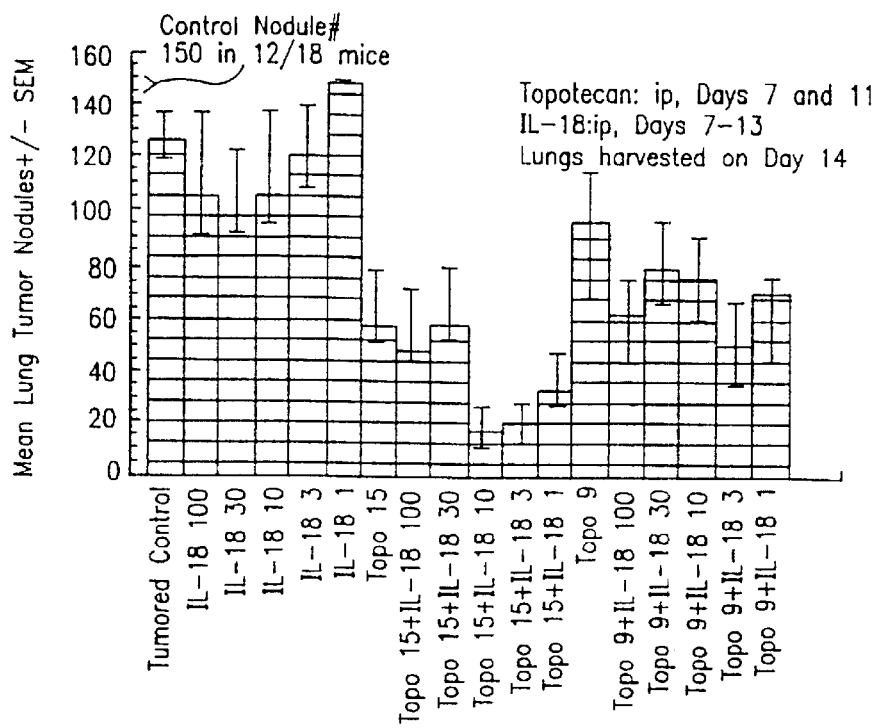
FIG. 3 is a graph illustrating the effect of IL-18 together with topotecan in reducing the number of pulmonary tumor nodules (confirmation experiment).
Figure 4:
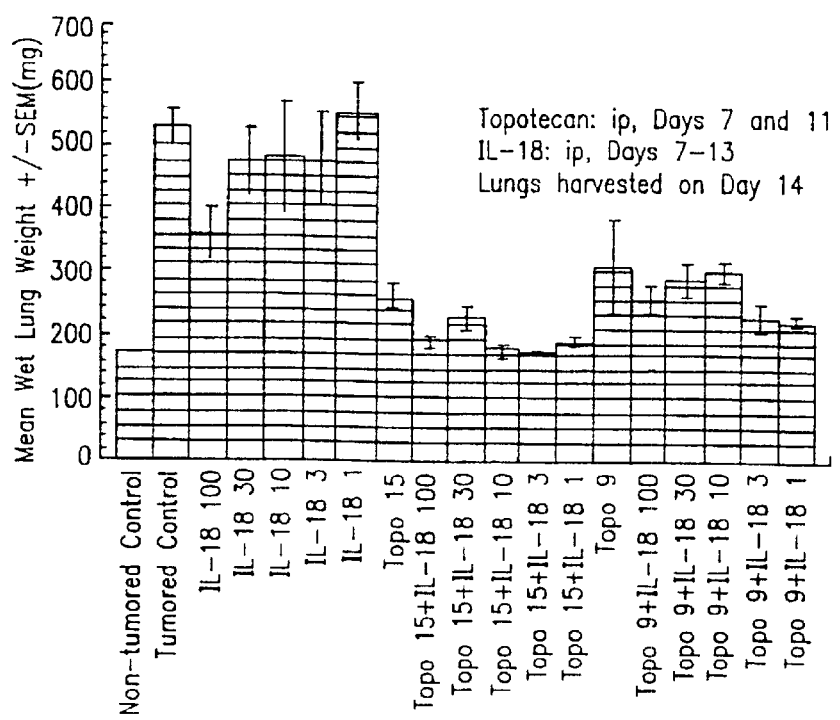
FIG. 4 is a graph illustrating the effect of IL-18 in combination with topotecan in reducing pulmonary tumor growth (confirmation experiment).

In a further experiment, the activity of the combination of the topotecan plus IL-18 was confirmed in the advanced systemic Lewis lung carcinoma model. This experiment included the use of higher doses of IL-18. B6D2F$_1$ female mice (22–24 gm) were inoculated intravenously with $10^5$ Lewis lung carcinoma cells and were randomized to treatment groups of 12–14 mice each on Day 7; half of the mice in each group were killed on Day 14 to determine effects of treatment on pulmonary tumor growth, including tumor weight and nodule count. The remaining mice were continued under treatment and monitored for survival. Topotecan was administered intraperitonealy q4D×6 on Days 7, 11, 15, 19, 23, and 29; dosage levels shown are mg/kg. Murine IL-18 was administered intraperitonealy qD×26 from Day 7 to Day 33; dosage levels shown are μg/mouse. There were three groups of controls, all of which died between Day 14 and Day 28. (See FIGS. 3 and 4 and Table 2).

Results

The MTD of topotecan gave a good reduction in tumor weight and nodule count and there was a lesser effect on both parameters at the lower dose of topotecan. The combination reduced tumor burden below that achieved by topotecan alone. This was best evident in the tumor weight rather than the nodule count where there was a greater effect at lower doses of IL-18. This confirms the positive result seen in the initial study of this combination in Lewis lung carcinoma. (See FIGS. 3 and 4).

EXAMPLE II (B)

Survival in Lewis Lung Carcinoma Model

Experimental Protocol
See protocol for Example II (A).
Results

The results regarding the survival half of the experiment are summarized in Table 2 below. At the MTD of topotecan, there was a significantly longer survival time for the mice that also received IL-18. At the suboptimal topotecan dose there was a doubling of the lifespan prolongation at the highest dose of IL-18.

TABLE 2

| Treatment | Dosage Level* | n | Median Survival Time (Days) | Increase in Lifespan (%) |
|---|---|---|---|---|
| Tumor Control |  | 18 | 18 |  |
| IL-18 | 100 | 6 | 22 | 22 |
|  | 30 | 6 | 18.5 | 3 |
|  | 10 | 6 | 18 | 0 |
|  | 3 | 6 | 18 | 0 |
|  | 1 | 6 | 20 | 11 |
| Topotecan | 15 | 6 | 33.5 | 86 |
| Topotecan + IL-18 | 15 + 100 | 7 | 43 | 139 |
|  | 15 + 30 | 7 | 42 | 133 |
|  | 15 + 10 | 7 | 41 | 128 |
|  | 15 + 2 | 7 | 42 | 133 |
|  | 15 + 1 | 6 | 38 | 111 |
| Topotecan | 9 | 6 | 25.5 | 42 |
| Topotecan + IL-18 | 9 + 100 | 7 | 34 | 89 |
|  | 9 + 30 | 7 | 30 | 67 |
|  | 9 + 10 | 7 | 27 | 50 |
|  | 9 + 3 | 7 | 30 | 67 |
|  | 9 + 1 | 7 | 29 | 61 |

Topotecan was administered intraperitonealy q4D × 6 on Days 7, 11, 15, 19, 23, and 29; dosage levels shown are mg/kg.
Murine IL-18 was administered intraperitonealy qD × 26 from Day 7 to Day 33; dosage levels shown are μg/mouse.

EXAMPLE III

MOPC-315 Plasmacytoma

Experimental Protocol

The MOPC-315 plasmacytoma is analogous to the human cancer known as multiple myeloma. This tumor is a malignancy of the plasma cells, a mature form of B lymphocytes involved in antibody expression. MOPC-315 grows rapidly to a very large size in syngeneic BALB/c mice. It is not highly metastatic or invasive.

Figure 5:
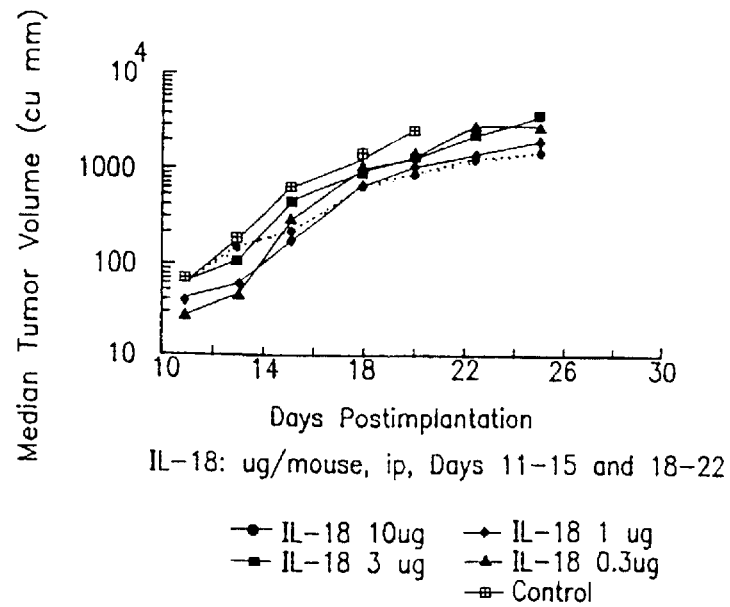
FIG. 5 is a graph illustrating the effect of low dose IL-18 on growth of advanced subcutaneously implanted MOPC-315 plasmacytoma in female BALB/c mice.
Figure 6:
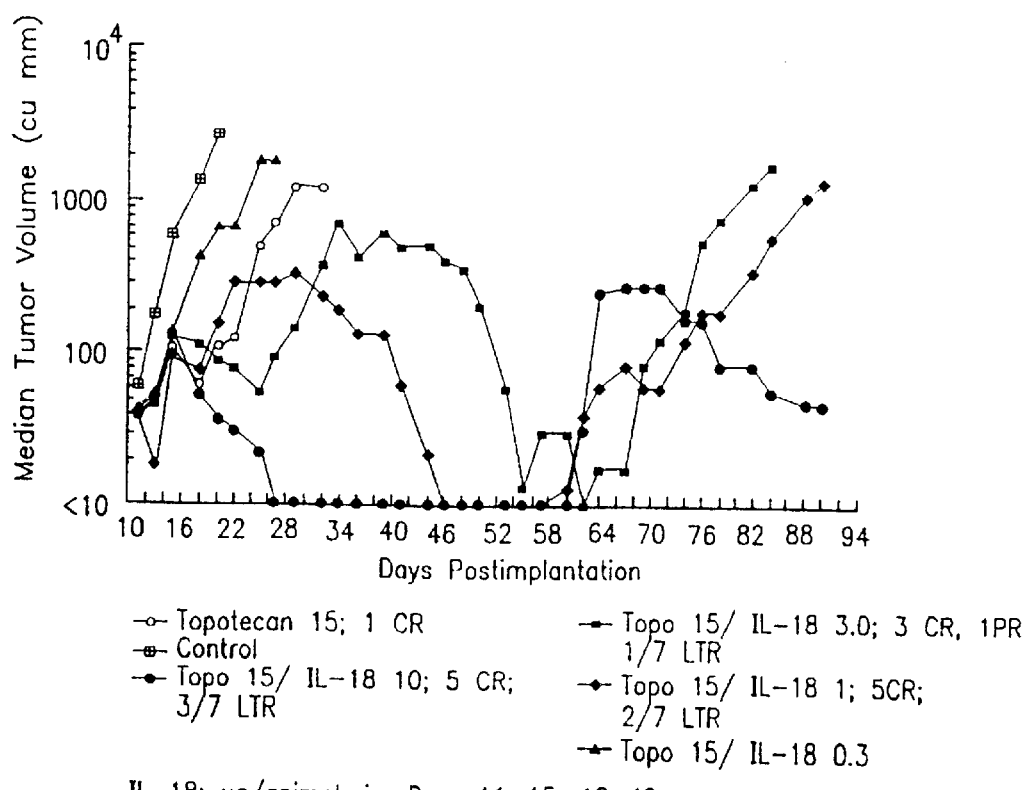
FIG. 6 is a graph illustrating the combined effect of IL-18 with an MTD of topotecan in advanced MOPC-315 plasmacytoma.
Figure 7:
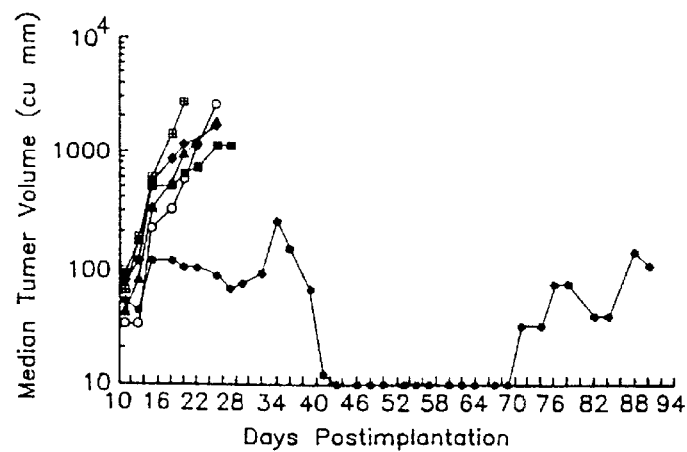
FIG. 7 is a graph illustrating the combined effect of IL-18 with a suboptimal dose of topotecan in advanced MOPC-315 plasmacytoma.

IL-18 was evaluated in mice bearing established subcutaneous MOPC-315 plasmacytoma. In order to increase chances of seeing an effect of immunotherapy, IL-18 was evaluated in combination with an effective chemotherapeutic agent as well as by monotherapy. IL-18 at 0.3, 1, 3, and 10 μg/mouse was administered daily intraperitonealy and topotecan was administered intraperitonealy on a q4D schedule at 9 and 15 mg/kg. Both drugs were started on Day 11 postimplantation when the median tumor volume ranged from 32 to 88 mg. Control tumors took 17.2 days to grow to 1 gram. (See FIGS. 5–7).

Results

IL-18 treatment alone had only a minimal effect on the tumor growth of established tumors at the doses evaluated in this experiment. Tumor growth was delayed by 1.3–3.1 days. (See FIG. 5.). Topotecan alone produced 1/7 complete regressions at its MTD and delayed tumor growth by about 12 days. The combination of the MTD of topotecan+IL-18 at 10, 3 or 1 μg/mouse/day was considerably more active than topotecan alone with complete regression in up to 5/7 mice and long-term regressions. Remarkably, tumors grew to quite large size before regressing. Also quite notable is that tumors re-grew after discontinuation of treatment and then regressed again in the absence of further therapy, suggesting an immune-mediated response. (See FIG. 6).

IL-18 also demonstrated enhanced and unexpected results with a suboptimal dose of topotecan. At 9 mg/kg topotecan had little or no effect on tumor growth with no regressions and only a 4-day tumor growth delay. With the high dose of IL-18, there were 5 complete regressions and 1 PR out of 7 mice. Two of these were long-term regressions still evident at 94 days. (See FIG. 7).

EXAMPLE IV

MOPC-315 Plasmacytoma

Experimental Protocol

The activity of IL-18 in combination with topotecan in mice bearing advanced MOPC-315 plasmacytoma was confirmed in a large experiment in which higher doses of IL-18 were used. In this experiment, topotecan was administered q4D×6 beginning on Day 10 and IL-18 was given qD×30 beginning on the same day. Both drugs were administered intraperitonealy and activity was assessed by tumor measurements.

Results

Figure 8:
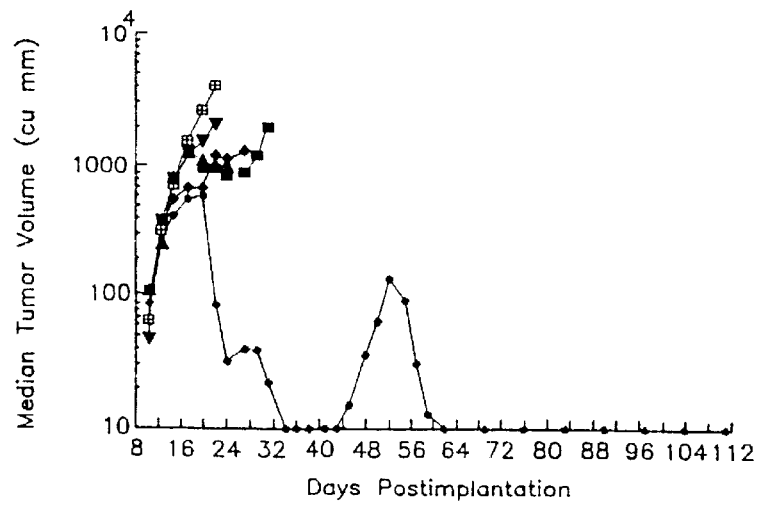
FIG. 8 is a graph illustrating the effect of high-dose IL-18 on advanced subcutaneous MOPC-315 plasmacytoma.

In the prior experiment in which IL-18 was administered at a top dose of 10 μg/mouse/day, there was no effect of IL-18 alone on tumor growth. However, in the confirmatory trial, IL-18 was given at higher doses, 100 and 30 μg/mouse/day, and at the highest dose was effective alone in inducing delayed tumor regression with 4 of 6 complete regressions. Lower doses of IL-18 were ineffective as shown in FIG. 8.

Figure 9:
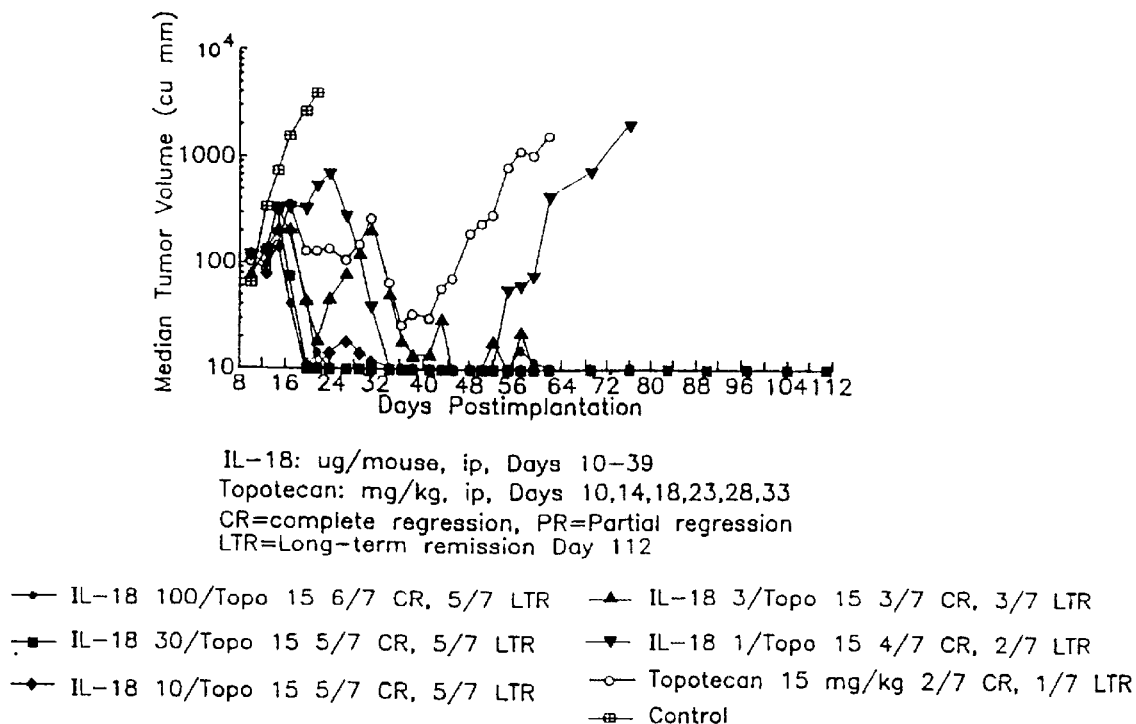
FIG. 9 is a graph illustrating the effect of combining IL-18 with topotecan against advanced subcutaneous MOPC-315 plasmacytoma (confirmation experiment).

The highly effective activity of the combination of IL-18 with topotecan at the MTD of topotecan was confirmed. (See FIG. 9). Topotecan alone was quite effective, producing 2/6 complete regressions and protracted inhibition of tumor growth. Re-growth, however, was evident upon discontinuation of topotecan on Day 33. At the top three doses of IL-18 there was a rapid, complete and protracted regression in virtually all of the treated mice. These responses occurred at dose levels of IL-18 that were ineffective when used alone. (See FIG. 9).

Figure 10:
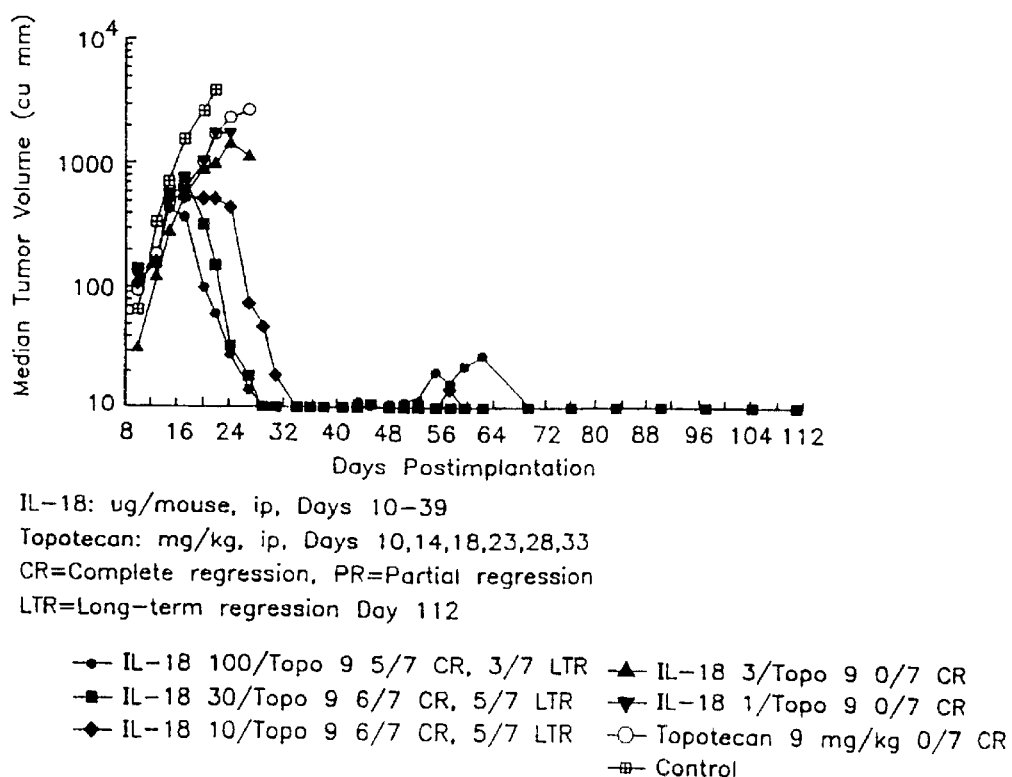
FIG. 10 is a graph illustrating the effect of combining IL-18 with a suboptimal dose of topotecan against advanced subcutaneous MOPC-315 plasmacytoma (confirmation experiment).

A suboptimal dose of topotecan had virtually no effect on this advanced tumor while there were complete regressions in almost all animals at the top three doses of the IL-18 combination. (See FIG. 10).

EXAMPLE V

MOPC-315 Plasmacytoma (Schedule and Route Study)

Experimental Protocol

Figure 11:
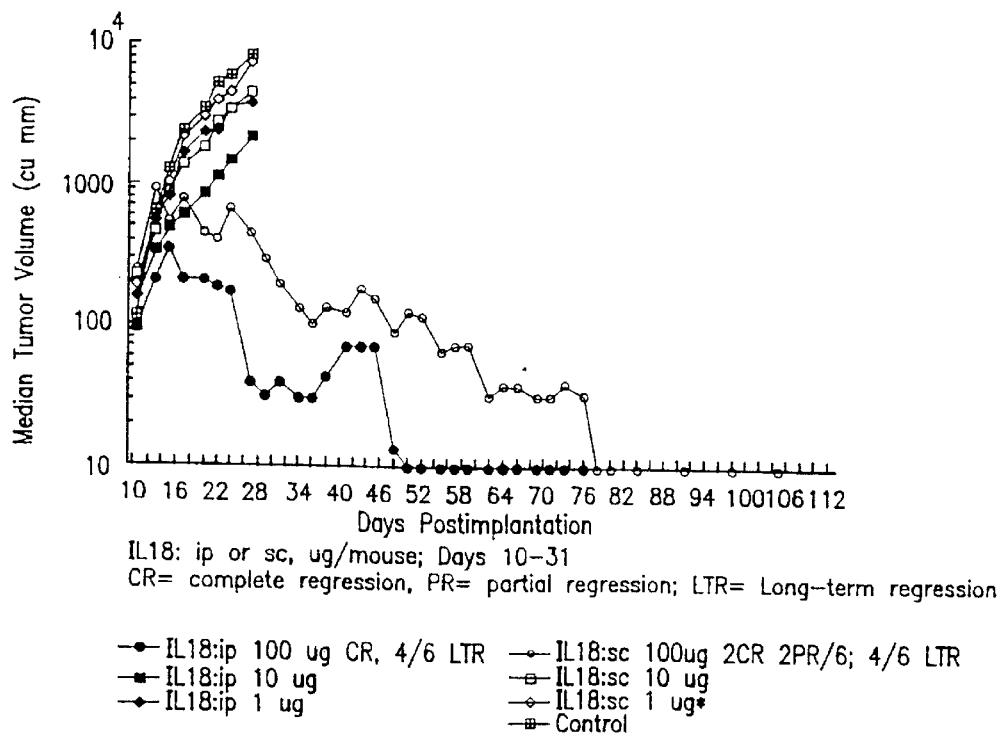
FIG. 11 is graph illustrating the effect of combining high-dose IL-18 intraperitonealy or subcutaneously as a single agent on advanced subcutaneous MOPC-315 plasmacytoma.
Figure 12:
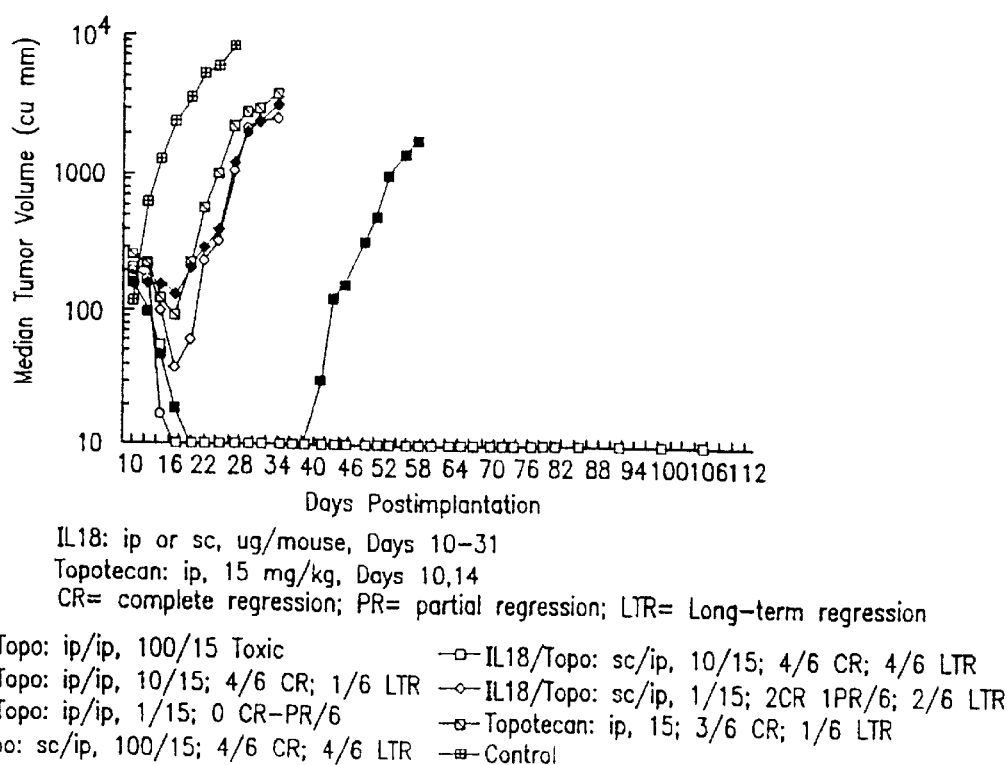
FIG. 12 is a graph illustrating the effect of IL-18 when given intraperitonealy or subcutaneously in combination with topotecan against subcutaneous MOPC-315 plasmacytoma.

The evaluation of IL-18 in combination with chemotherapy was repeated to establish: (a) how effective is IL-18 in tumor models when given subcutaneously and (b) whether IL-18 is active when given on an intermittent schedule or whether daily treatment is necessary. The experiment was set up again with topotecan in the advanced MOPC-315 plasmacytoma model with treatment starting on Day 10 when tumors were about 100 mm$^3$ in volume. Topotecan was given at its MTD of 15 mg/kg on a q4D regimen and IL-18 was given over a broad dosage range either intraperitonealy or subcutaneously on a q1D or q4D regimen. In this experiment, there was more toxicity seen with the combination than in previous studies as was evident from severe weight loss so the topotecan was stopped after only two courses. However, IL-18 was continued. (See FIGS. 11–13).

Results

Figure 13:
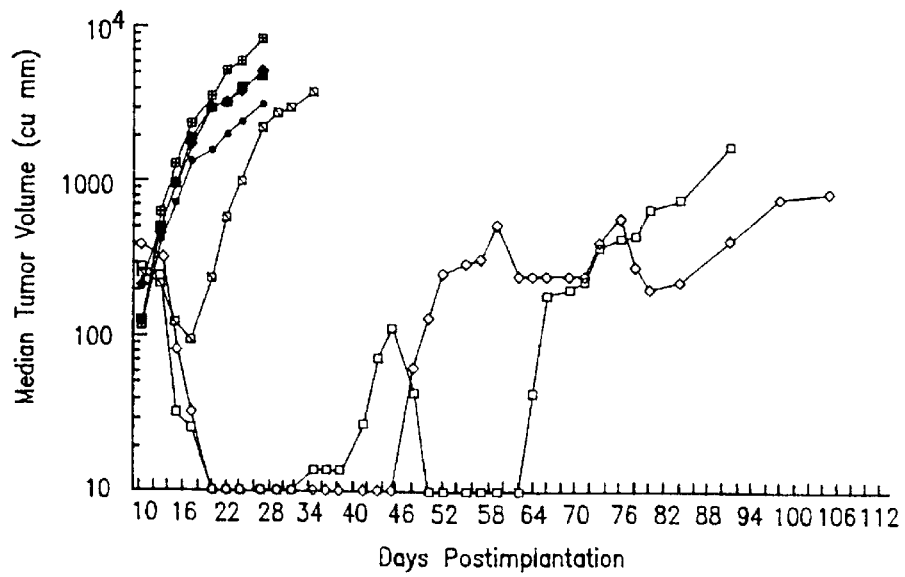
FIG. 13 is a graph illustrating the effect of intermittent subcutaneously administered IL-18 combination with topotecan against advanced subcutaneous MOPC-315 plasmacytoma.

IL-18 alone was active on the q1D schedule at the 100 μg/day dose level, confirming results of the earlier experiment. Activity was seen for both intraperitoneal and subcutaneous routes, although intraperitoneal was more effective. (See FIG. 11). As shown in FIG. 13, intermittent IL-18 at 1000 or 100 μg/dose was ineffective in inducing regression when the cytokine was used alone.

The activity of daily IL-18 in combination with topotecan was again confirmed and there was equivalent activity when IL-18 was given subcutaneously or intraperitonealy. By either route, doses of 10 μg/day or higher were required to show the enhanced effect. (See FIG. 12).

The administration of IL-18 on an intermittent schedule was just as effective in combination with chemotherapy. The same doses of 10 or 100 μg/mouse/dose were effective on the q4D regimen as on the q1D regimen. (See FIG. 13).

EXAMPLE VI

B16 Melanoma

Experimental Protocol

In this experiment, IL-18 was evaluated in an advanced syngeneic tumor model alone and in combination with chemotherapy. Mice bearing advanced subcutaneous B16F10 melanoma were treated with IL-18 alone or in combination with either cyclophosphamide or topotecan. Treatment was initiated on Day 11 postimplantation. Vehicle controls had a median survival time of 20 days.

Results

Figure 14:
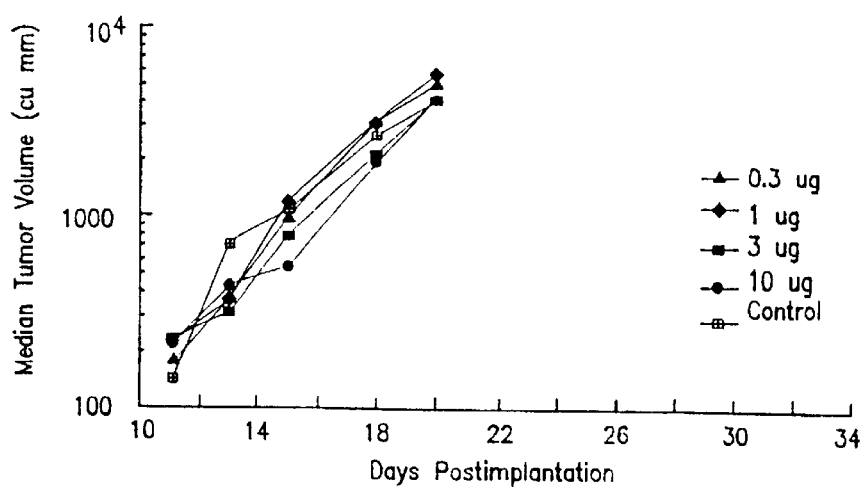
FIG. 14 is a graph illustrating the effect of IL-18 in inhibiting tumor growth of advanced subcutaneous B16F10 melanoma.
Figure 15:
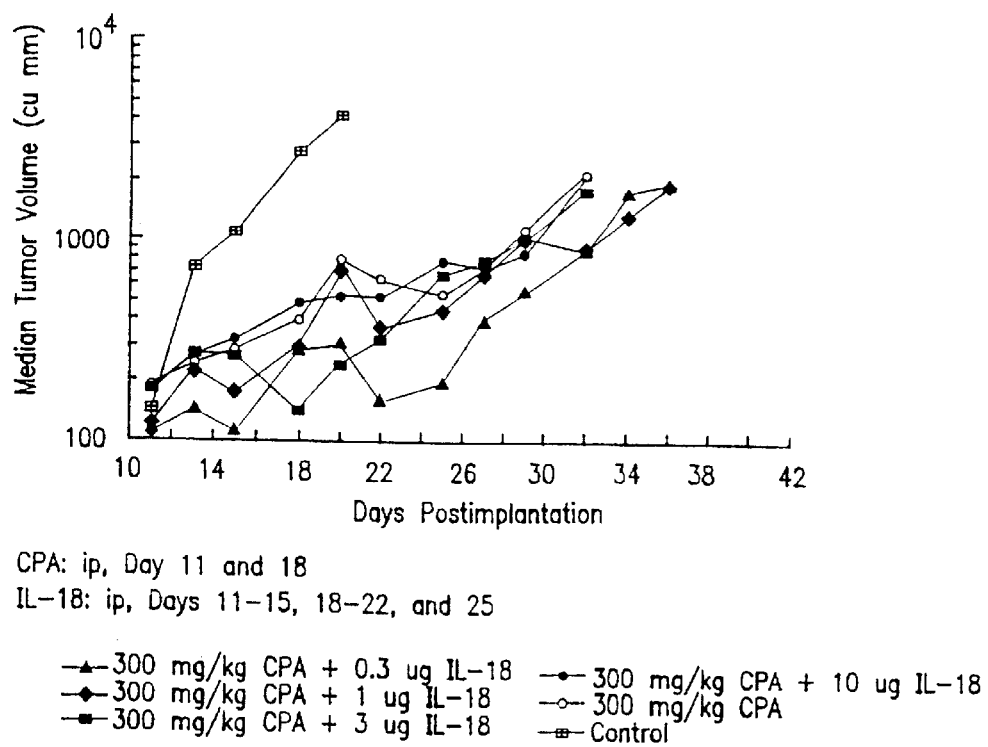
FIG. 15 is a graph illustrating the effect of IL-18 in prolonging the growth delay induced by cyclophosphamide in advanced subcutaneous B16F10 melanoma.
Figure 16:
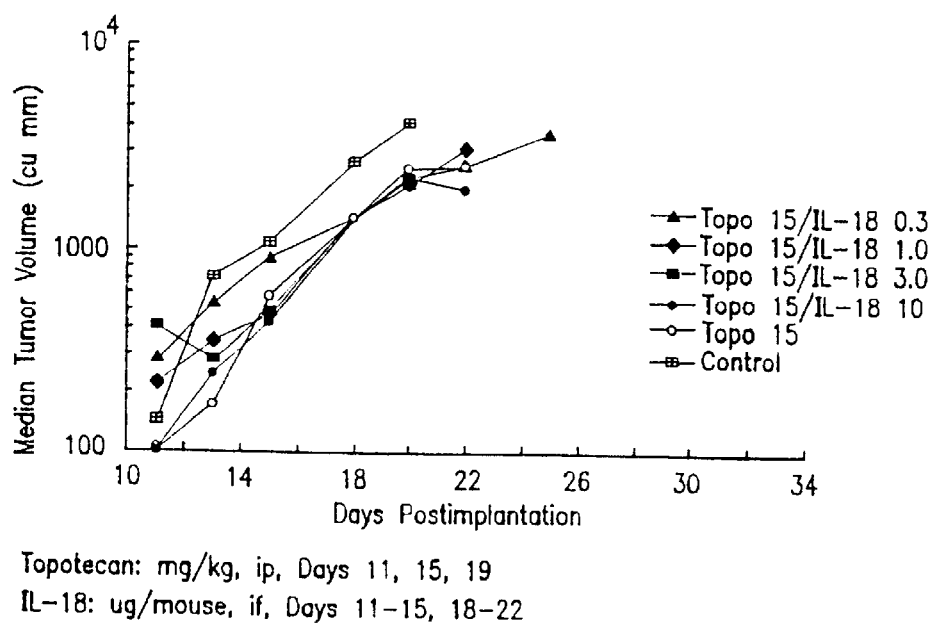
FIG. 16 is a graph illustrating the effect of topotecan alone or in combination with IL-18 in mice bearing advanced subcutaneous B16F10 melanoma.

IL-18 treatment alone had no effect on tumor growth and had a minimal effect on survival time (<30% ILS), although it should be noted that IL-18 was not tested at the high dose that proved to be active alone in the plasmacytoma model. (See FIG. 14). An MTD of cyclophosphamide, 300 mg/kg given on the q7D schedule, increased survival by 95% produced a tumor growth delay of 14 days. (See FIG. 15). Topotecan was inactive at its MTD. (See FIG. 16).

The combination of IL-18 with the MTD of cyclophosphamide had a minimal and dose-independent effect on antitumor activity. The lowest dose of IL-18 with cyclophosphamide prolonged lifespan by 110% and produced an additional 3 days of tumor growth delay. Higher IL-18 dose combinations were not different from cyclophosphamide alone. (See FIG. 15).

The combination of an MTD of topotecan with IL-18 was no more effective than topotecan alone in delaying growth of B16F10 or prolonging lifespan in this metastatic tumor model. (See FIG. 16). It should be noted that B16F10 melanoma is a vigorous tumor model which responds poorly to currently available therapeutic approaches.

EXAMPLE VII

B16 Melanoma

Experimental Protocol

A repeat experiment was conducted to determine the effectiveness of IL-18 in combination with cyclophosphamide in the B16 melanoma tumor model. The B16F10 subline was implanted subcutaneously from tissue culture and allowed to grow to a median of 100 mm³ before treatment. There was delayed growth of tumor in this experiment such that a median of 100 mm³ was not reached until Day 14; there was also a wide variance in tumor size with some animals having very large tumors at the initiation of treatment.

Results

Figure 17:
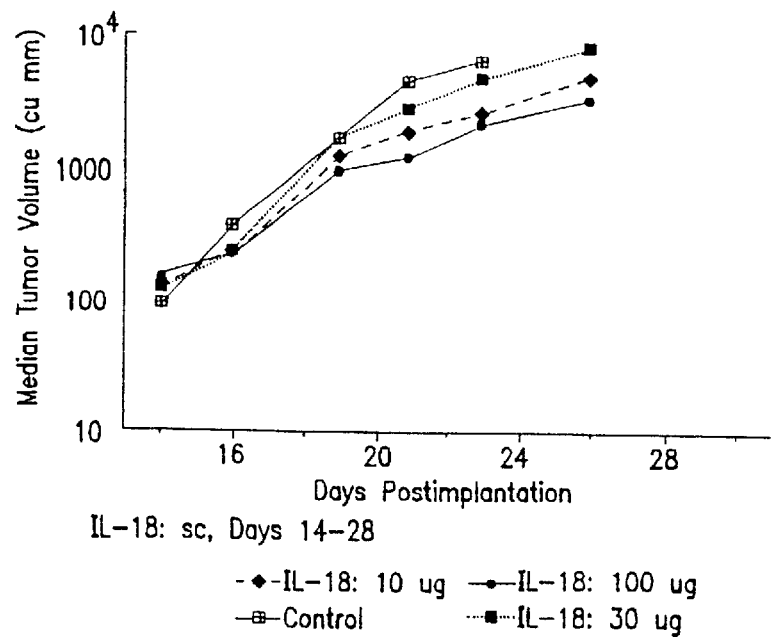
FIG. 17 is a graph illustrating the effect of high dose IL-18 alone in inhibiting tumor growth of advanced subcutaneous B16F10 melanoma.
Figure 18:
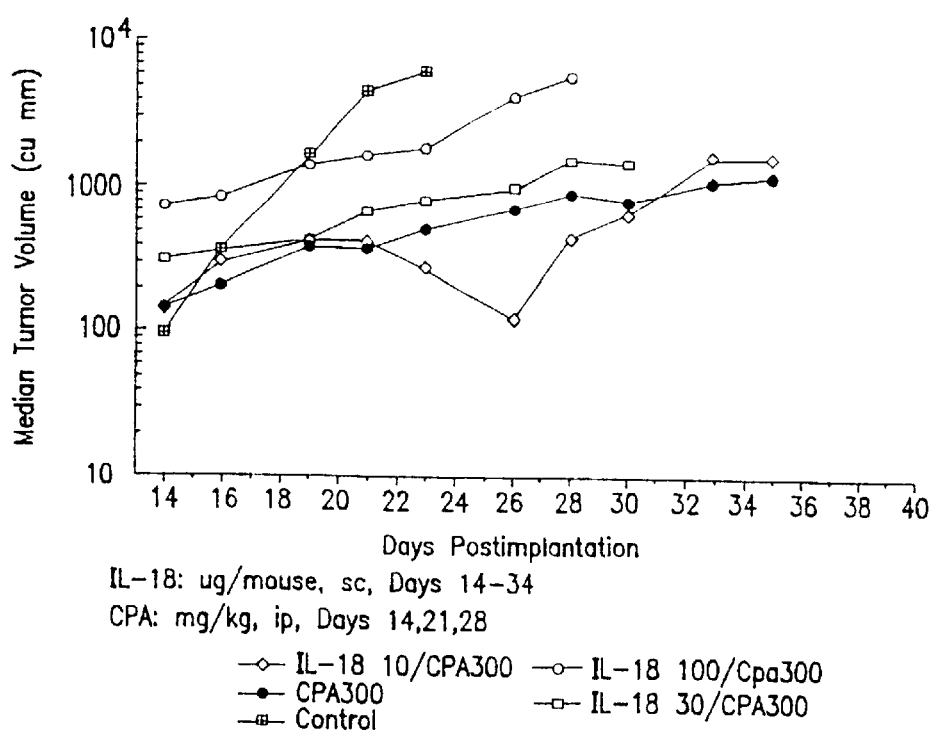
FIG. 18 is a graph illustrating the effect of IL-18 in combination with an MTD of cyclophosphamide in advanced subcutaneous B16F10 melanoma (confirmation experiment).
Figure 19:
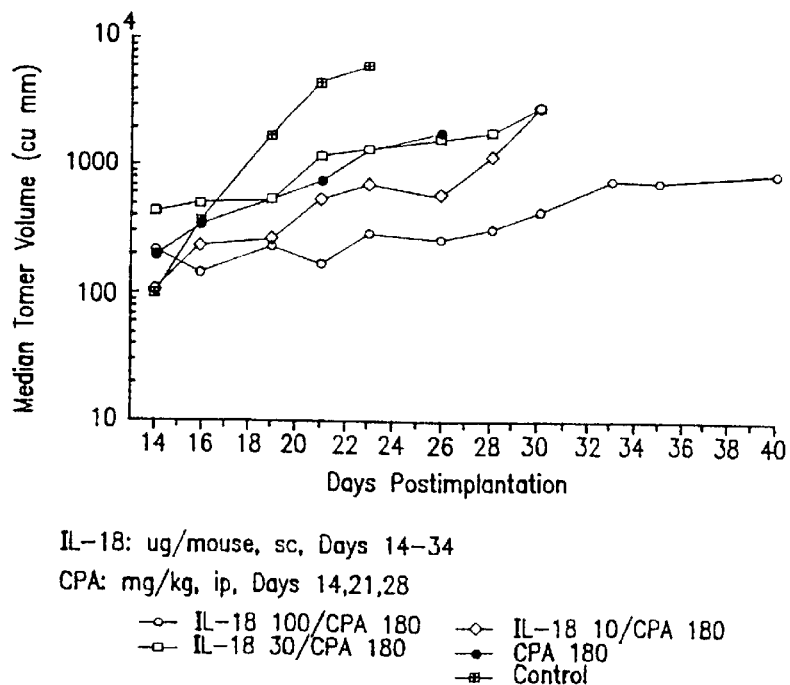
FIG. 19 is a graph illustrating the effect of IL-18 in combination with a suboptimal dose of cyclophosphamide in advanced subcutaneous B16F10 melanoma.

There were no regressions with either IL-18, cyclophosphamide or the combination. IL-18 alone produced a minimal tumor growth delay of about 2 days. The MTD of cyclophosphamide delayed tumor growth by 14 days and the addition of IL-18 did not have much of an effect on this activity. At the high dose of IL-18 in combination, there was an apparently reduced effect but this is solely due to the fact that the tumors were much larger in this group at initiation of therapy. However, at the suboptimal dose of cyclophosphamide, 180 mg/kg, which delayed tumor growth by only 4 days, there was a positive effect with the combination, with tumor growth delays extended to about 10 and 15 days except for that combination group that had large tumors at the start of therapy. (See FIGS. 17–19).

EXAMPLE VIII

Madison 109 Lung Carcinoma

Experimental Protocol

An experiment was conducted to determine the effectiveness of IL-18 in combination with paclitaxel in the Madison 109 lung tumor model. This tumor model is the most paclitaxel-sensitive syngeneic murine tumor, but is, nevertheless, only modestly responsive to the drug. The tumor was implanted subcutaneously and allowed to grow to a median of 126–326 mm³ before treatment. There was wide variance in tumor size with some animals having very large tumors at the initiation of treatment. Paclitaxel (12, 24, 48 mg/kg) was administered intravenously on a qD×5 schedule (Days 9–13). IL-18 was administered subcutaneously on a qD×21 schedule at 1, 10 and 100 µg per mouse.

Results

Figure 20:
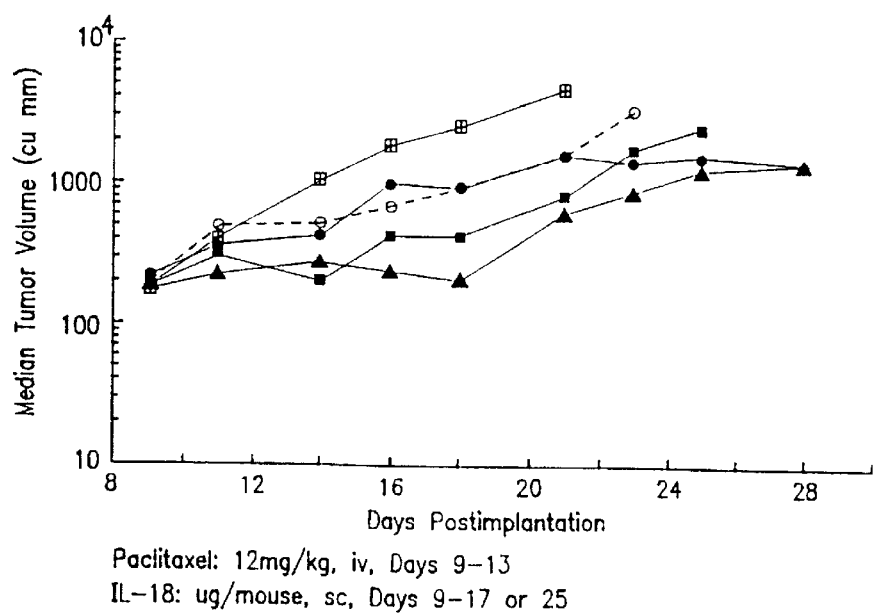
FIG. 20 is a graph illustrating the effect of IL-18 in combination with paclitaxel in advanced subcutaneous Madison lung carcinoma.

Paclitaxel was toxic at 48 mg/kg alone and in combination and was close to being toxic at 24 mg/kg based on excessive weight loss. Addition of the higher doses of IL-18 at this paclitaxel dose resulted in early deaths. IL-18 alone was well-tolerated as in earlier experiments. (See FIG. 20 and Table 3).

There were no regressions with either treatment alone or with the combination. Paclitaxel alone produced minimal tumor growth delay and minimal prolongation of survival. There was no major improvement in efficacy with the combination, however, at the 12 mg/kg dose of paclitaxel there was a prolongation of tumor growth delay with the lower doses of IL-18. IL-18 alone at the low dose prolonged lifespan by 77% without delaying tumor growth. This same lifespan prolongation was seen when this dose of IL-18 was combined with paclitaxel. (See FIG. 20 and Table 3).

TABLE 3

| IL-18 | Paclitaxel mg/kg, iv | | | |
|---|---|---|---|---|
| µg, sc | 0 | 12 | 24 | 48 |
| 0 | | T-C 3.5 days, NT 27% ILS | T-C 9.7 days, 4.7 g 35% ILS | Toxic |
| 1 | T-C 1.7 days, NT 77% ILS | T-C 9.9 days, −3.7 g 77% ILS | T-C 9.7 days, −5.6 g 77% ILS | Toxic |
| 10 | T-C 2.1 days, NT 12% ILS | T-C 6.4 days, −4.2 g 21% ILS | Toxic | Toxic |
| 100 | T-C 2.8 days, NT 0% ILS | T-C 3.3 days, −3.5 g 46% ILS | Toxic | Toxic |

T-C: tumor growth delay
NT: not toxic, less than 3 gm of body weight loss

EXAMPLE IX

Mammary Adenocarcinoma 16/C

Experimental Protocol

An experiment was conducted to determine the effectiveness of IL-18 on its own and in combination with doxorubicin in the 16/c mammary adenocarcinoma tumor model. The 16/c line was implanted subcutaneously at a 1:10 brei and allowed to grow to a median of 52–109 mm³ before initiation of treatment. Doxorubicin was administered intravenously on Days 12 and 19 at 7.2, 12, and 20 mg/kg. IL-18 was administered subcutaneously at 1, 10, and 100 µg/mouse on a qD×21 schedule starting from Day 12. The endpoints of this study were tumor growth delay and regression.

Results

There were no regressions with either doxorubicin or IL-18 alone or with the combination. As shown in Table 4, IL-18 markedly exacerbated the toxicity of doxorubicin. The MTD of doxorubicin was 20 mg/kg. This dose was toxic even when combined with 1 µg of IL-18. At 1/3 of its MTD, a dose of doxorubicin that produced no weight loss and had little or no efficacy, there was toxicity with IL-18 at 10 or 100 µg.

TABLE 4

| IL-18 | Doxorubicin mg/kg, iv | | | |
|---|---|---|---|---|
| µg/mouse, ip | 0 | 7.2 | 12 | 20 |
| 0 | | Not Toxic | Not Toxic | Not Toxic |
| 1 | Not Toxic | Not Toxic (1/6) | Toxic (4/6) | Toxic (4/6) |
| 10 | Not Toxic | Toxic (5/6) | Toxic (5/6) | Toxic (6/6) |
| 100 | Not Toxic | Toxic (6/6) | Toxic (5/6) | Toxic (6/6) |

(toxic deaths)

Figure 21:
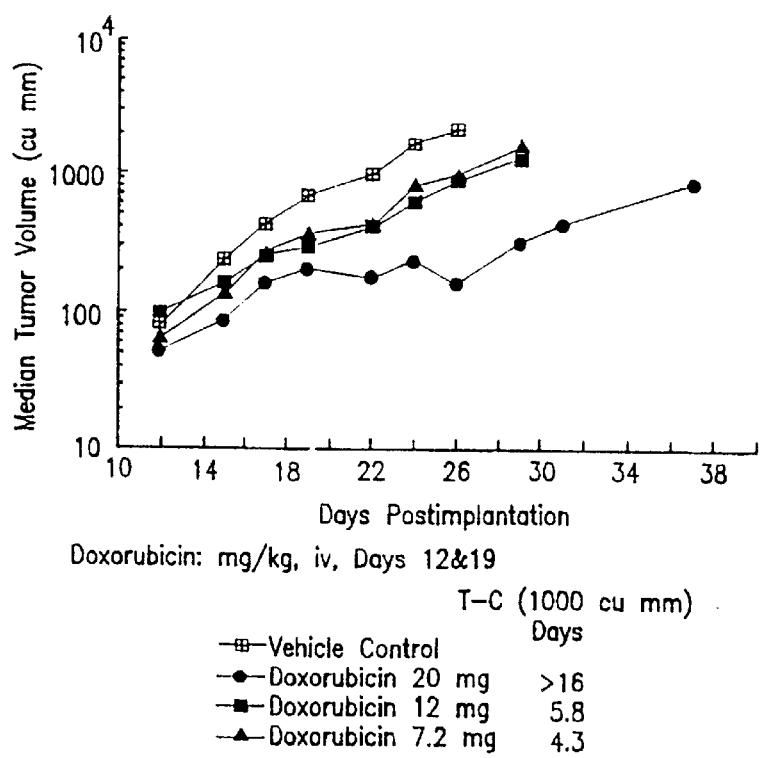
FIG. 21 is a graph illustrating the effect of doxorubicin in producing dose-dependent delay of growth of advanced mammary adenocarcinoma 16/c.
Figure 22:
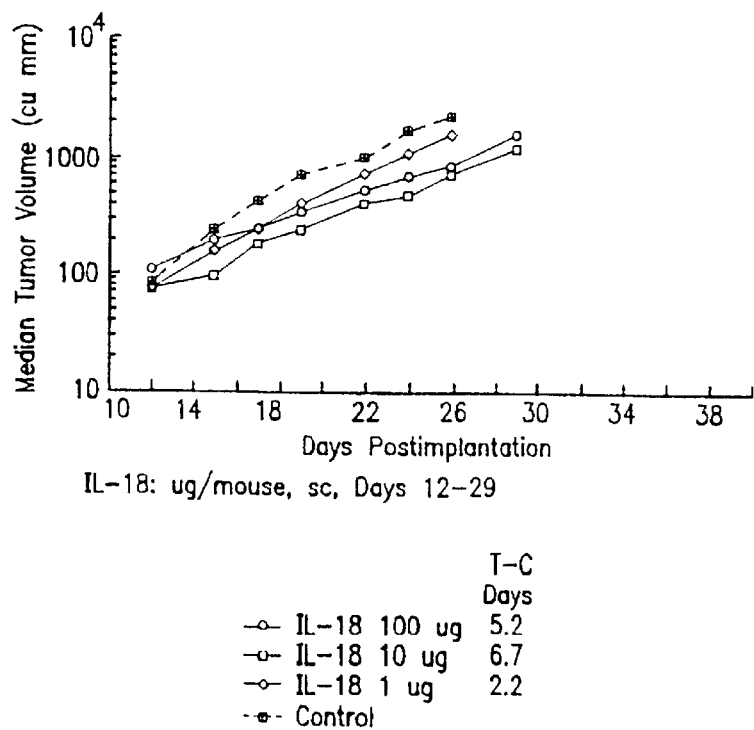
FIG. 22 is a graph illustrating the effect of IL-18 in producing minimal tumor growth delay of advanced mammary adenocarcinoma 16/c.
Figure 23:
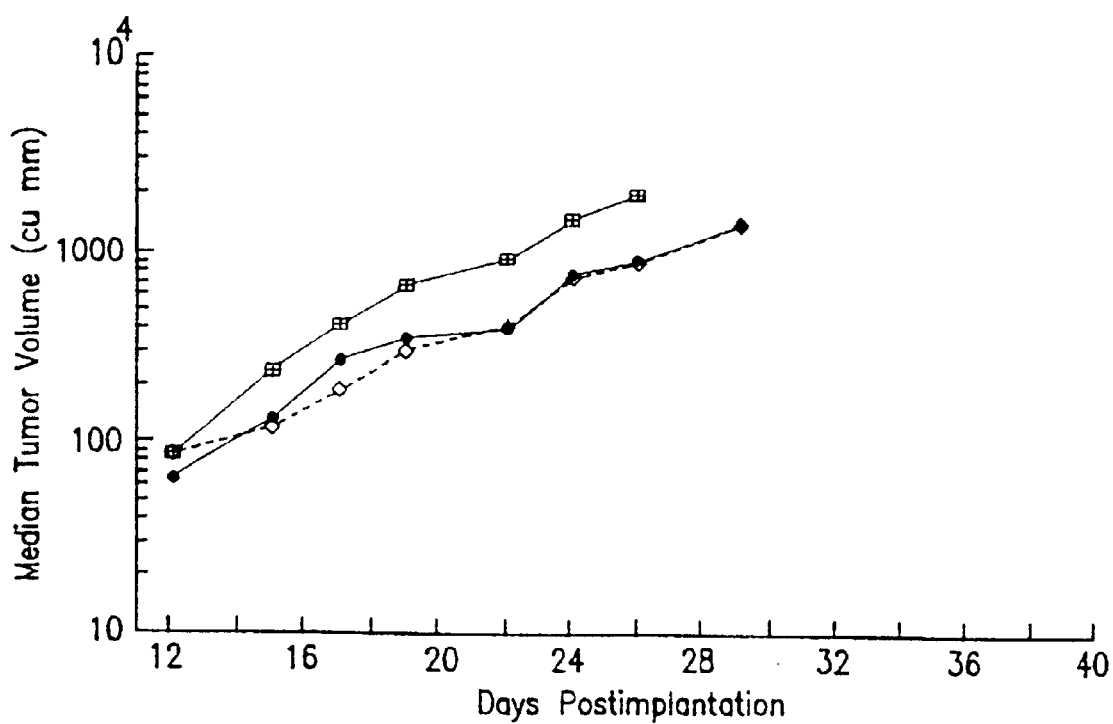
FIG. 23 is a graph illustrating the effect of IL-18 on the activity of doxorubicin in advanced mammary adenocarcinoma 16/c.

Because of toxicity, the effect of the combination with respect to antitumor activity could not be determined. Doxorubicin produced a dose-dependent tumor growth delay as shown in FIG. 21. IL-18 alone produced a minimal tumor growth delay of less than a week, with no dose-response evident over the 100-fold dose range evaluated. (See FIG. 22). At the lowest dose of both agents, the only dose of the combination that was tolerated, there was no enhancement of the antitumor effect of doxorubicin. (See FIG. 23).

What is claimed is:

1. A pharmaceutical composition comprising the polypeptide having the amino acid sequence of SEQ ID NO:1, in combination with topotecan.

2. The pharmaceutical composition as claimed in claim 1, wherein said pharmaceutical composition further comprises a pharmaceutically acceptable carrier.

3. A process for preparing the composition as claimed in claim 1, said process comprising the steps of:
   (a) combining the polypeptide with topotecan; and
   (b) recovering the resulting composition.

4. A method of treating cancer in a mammal, comprising administering to the mammal a cancer-inhibiting amount of the pharmaceutical composition as claimed in claim 2.

5. A method of inhibiting the growth of tumor cells in a mammal sensitive to the pharmaceutical composition as claimed in claim 2, wherein said method comprises administering to the mammal afflicted with said tumor cells, an effective, tumor cell growth-inhibiting amount of said composition.

* * * * *

SEQUENCE LISTING

<160> NUMBER OF SEQ ID NOS: 2

<210> SEQ ID NO 1
<211> LENGTH: 157
<212> TYPE: PRT
<213> ORGANISM: Human

<400> SEQUENCE: 1

```
Tyr Phe Gly Lys Leu Glu Ser Lys Leu Ser Val Ile Arg Asn Leu Asn
 1               5                  10                  15

Asp Gln Val Leu Phe Ile Asp Gln Gly Asn Arg Pro Leu Phe Glu Asp
             20                  25                  30

Met Thr Asp Ser Asp Cys Arg Asp Asn Ala Pro Arg Thr Ile Phe Ile
         35                  40                  45

Ile Ser Met Tyr Lys Asp Ser Gln Pro Arg Gly Met Ala Val Thr Ile
     50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
            115                 120                 125

Lys Glu Arg Asp Leu Phe Lys Leu Ile Leu Lys Lys Glu Asp Glu Leu
        130                 135                 140

Gly Asp Arg Ser Ile Met Phe Thr Val Gln Asn Glu Asp
145                 150                 155
```

<210> SEQ ID NO 2
<211> LENGTH: 157
<212> TYPE: PRT
<213> ORGANISM: Mouse

<400> SEQUENCE: 2

```
Asn Phe Gly Arg Leu His Cys Thr Thr Ala Val Ile Arg Asn Ile Asn
 1               5                  10                  15

Asp Gln Val Leu Phe Val Asp Lys Arg Gln Pro Val Phe Glu Asp Met
             20                  25                  30

Thr Asp Ile Asp Gln Ser Ala Ser Glu Pro Gln Thr Arg Leu Ile Ile
         35                  40                  45

Tyr Met Tyr Lys Asp Ser Glu Val Arg Gly Leu Ala Val Thr Leu Ser
     50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Ile Gln Ser
                 85                  90                  95

Asp Leu Ile Phe Phe Gln Lys Arg Val Pro Gly His Asn Lys Met Glu
                100                 105                 110

Phe Glu Ser Ser Leu Tyr Glu Gly His Phe Leu Ala Cys Gln Lys Glu
            115                 120                 125

Asp Asp Ala Phe Lys Leu Ile Leu Lys Lys Asp Glu Asn Gly Asp
        130                 135                 140

Lys Ser Val Met Phe Thr Leu Thr Asn Leu His Gln Ser
145                 150                 155
```